(12) United States Patent
Wempe et al.

(10) Patent No.: US 8,263,094 B2
(45) Date of Patent: Sep. 11, 2012

(54) ESTERS OF 4,5-DISUBSTITUTED-OXY-2-METHYL-3,6-DIOXO-CYCLOHEXA-1,4-DIENYL ALKYL ACIDS AND PREPARATION THEREOF

(75) Inventors: Michael Fitzpatrick Wempe, Kingsport, TN (US); Liu Deng, Kingsport, TN (US); Stephanie Kay Clendennen, Kingsport, TN (US); Neil Warren Boaz, Kingsport, TN (US)

(73) Assignee: Eastman Chemical Company, Kongsport, TN (US)

( * ) Notice: Subject to any disclaimer, the term of this patent is extended or adjusted under 35 U.S.C. 154(b) by 1023 days.

(21) Appl. No.: 12/236,171

(22) Filed: Sep. 23, 2008

(65) Prior Publication Data

US 2010/0076077 A1    Mar. 25, 2010

(51) Int. Cl.
*A61K 8/02* (2006.01)
*C12P 33/20* (2006.01)
*C07D 487/00* (2006.01)

(52) U.S. Cl. .............. 424/401; 435/53; 532/1; 514/529

(58) Field of Classification Search .................. None
See application file for complete search history.

(56) References Cited

U.S. PATENT DOCUMENTS

| 4,388,312 | A | 6/1983 | Terao et al. |
|---|---|---|---|
| 4,393,075 | A | 7/1983 | Terao et al. |
| 4,495,104 | A | 1/1985 | Imada et al. |
| 4,533,554 | A | 8/1985 | Terao et al. |
| 4,559,177 | A | 12/1985 | Okutani et al. |
| 4,708,962 | A | 11/1987 | Higa et al. |
| 4,788,315 | A | 11/1988 | Kawabata |
| 4,803,268 | A | 2/1989 | Brunner et al. |
| 4,851,413 | A | 7/1989 | Terao et al. |
| 4,897,420 | A | 1/1990 | Watanabe et al. |
| 4,945,178 | A | 7/1990 | McCombs |
| 5,041,613 | A | 8/1991 | McCombs |
| 5,180,742 | A | 1/1993 | Terao et al. |
| 6,184,255 | B1 | 2/2001 | Mae et al. |
| 6,271,266 | B1 | 8/2001 | Miyamoto et al. |
| 6,756,045 | B1 | 6/2004 | Neudecker et al. |
| 2005/0148675 | A1 | 7/2005 | Lipshutz et al. |
| 2005/0175559 | A1 | 8/2005 | DiNardo et al. |
| 2005/0197407 | A1 | 9/2005 | DiNardo et al. |
| 2007/0072943 | A1 | 3/2007 | Miller et al. |
| 2009/0042271 | A1* | 2/2009 | Clendennen et al. ......... 435/198 |

FOREIGN PATENT DOCUMENTS

| DE | 10210854 | 9/2003 |
|---|---|---|
| EP | 0506159 | 9/1992 |
| EP | 0 719 552 A2 | 7/1996 |
| WO | 86/00887 | 8/1984 |

OTHER PUBLICATIONS

DeMarco, Federico et al.; "Cytotoxicity of dopamine-derived tetrahydroisoquinolines on melanoma cells"; Biochemical Pharmacology; 2002; pp. 1503-1512; 64.
Kojima, Hajime et al.; "Evaluation of skin irritation in a reconstituted human dermal model (3-D model) using water insoluble fatty acids, fatty alcohols and hydrocarbons"; Alternative Animal Test.Experiment; 1998; pp. 201-210; 5.
McDaniel, DH et al.; "Clinical efficacy assessment in photodamaged skin of 0.5% and 1.0% idebenone"; Journal of Cosmetic Dermatology; 2005; pp. 167-173; 4.
Okamoto, Kayoko et al.; "Effects of Q metabolites and related compounds on mitochondrial succinate and nadh oxidase systems"; Biochimica et Biophysica Acta; 1982; pp. 145-151; 682.
Okamoto, Kayoko et al.; "Synthesis of Quinones having Carboxy- and Hydroxy-Alkyl Side Chains, and Their Effects on Rat-Liver Lysosomal Membrane"; 1982; pp. 2797-2819; 30(8).
Schürer, N.Y.; "Implementation of fatty acid carriers to skin irritation and epidermal barrier"; Contact Dermatitis; 2002; pp. 199-205; 47.
Notification of Transmittal of the International Search Report and the Written Opinion of the International Searching Authority, or the Declaration date of mailing Jan. 13, 2010 received in corresponding International Application No. PCT/US2009/005183.

* cited by examiner

*Primary Examiner* — Lezah Roberts
*Assistant Examiner* — Nannette Holloman
(74) *Attorney, Agent, or Firm* — Jennifer R. Knight

(57) ABSTRACT

Esters of 4,5-disubstituted-oxy-2-methyl-3,6-dioxo-cyclohexa-1,4-dienyl alkyl acids were prepared chemically and/or enzymatically. Depending upon the ester, improved melanocyte cytotoxicity was achieved. Improved cytotoxicity characteristics are consistent with ester analogs being more physiologically compatible and less irritating to skin than their corresponding acids.

7 Claims, 1 Drawing Sheet

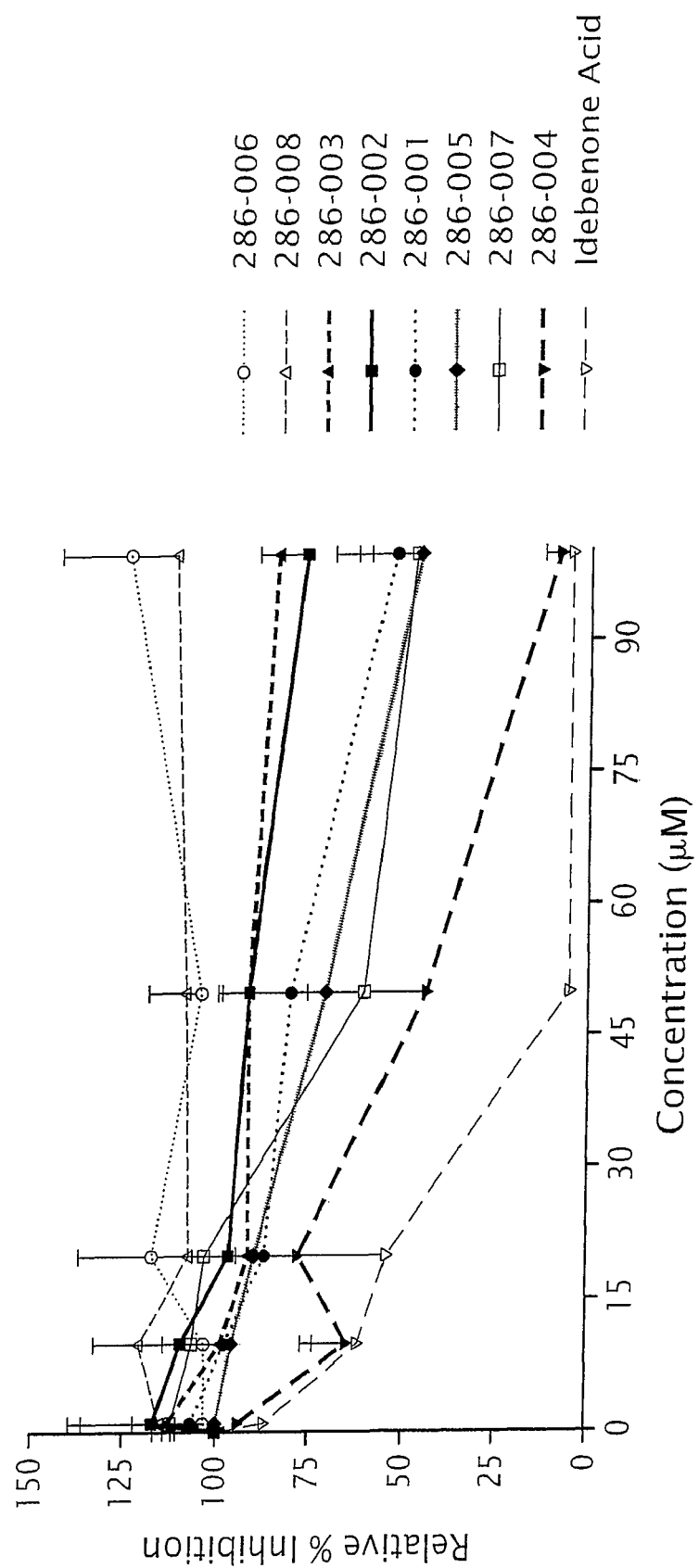

ESTERS OF 4,5-DISUBSTITUTED-OXY-2-METHYL-3,6-DIOXO-CYCLOHEXA-1,4-DIENYL ALKYL ACIDS AND PREPARATION THEREOF

FIELD OF THE INVENTION

The present invention relates to esters of 4,5-Disubstituted-oxy-methyl-3,6-dioxo-cyclohexa-1,4-dienyl alkyl acids, methods for preparing such esters, and composition which included such esters.

BACKGROUND

Long-chain alcohols have many uses in cosmetics and personal care. One such example is idebenone; a potent antioxidant shown to reduce skin roughness, fine lines and wrinkles. In addition, idebenone may improve photo-damaged skin (McDaniel, D. H. et al. *Journal of Cosmetic Dermatology* 2005, 4 (3), 167-173). This material has also been claimed to induce protective and regenerative effects (U.S. Pat. No. 6,756,045), reduce skin hyperpigmentation (US Patent Publication 2005/0175559), and to reduce irritation and/or inflammatory reaction in human skin (US Patent Application Publication 2005/0197407).

Idebenone (2-(10-hydroxydecyl)-5,6-dimethoxy-3-methylcyclohexa-2,5-diene-1,4-dione) can be oxidized to the corresponding acid (idebenone acid; 10-(4,5-dimethoxy-2-methyl-3,6-dioxocyclohexa-1,4-dienyl)decanoic acid). Ester derivatives of idebenone acid may improve the physical properties of this orange solid. In addition, depending upon the nature of the ester, esters of idebenone acid may or may not readily hydrolyze in the skin to afford idebenone acid along with the corresponding alcohol; depending upon the alcohol, hydrolysis product may be beneficial too.

The classical chemical preparation of esters such as idebenone acid esters involves either the reaction of an alcohol with the idebenone acid, an idebenone acid halide, or idebenone acid anhydride. Methods to prepare esters can be conducted using mild to harsh chemical methodology and/or via enzymatically. There are limited reports of short-chained idebenone acid esters (i.e. methyl, ethyl and benzyl; Okamoto, K. et al. *Chem. Pharm. Bull.* 1982, 8, 2797-2819; and Okamoto, K. et al., *Biochim. Biophys. Acta*. 1982, 682, 145-151). However, there lacks idebenone acid esters derived from longer-chained alcohols. A long-chain ester analog may be more physiologically compatible and less irritating to skin than idebenone acid (Schürer, 2002, *Contact Dematitis* 47: 199-205; Kojima et al., 1998, *Altern. Animal Test.* Exper. 5: 201-210). Hence, compositions based on esters of 4,5-disubstituted-oxy-2-methyl-3,6-dioxo-cyclohexa-1,4-dienyl alkyl acids may reduce unwanted side effects (i.e. skin irritation). It is the object of this invention to provide such compounds and compositions.

SUMMARY OF THE INVENTION

A first embodiment of the present invention concerns a composition, comprising an ester and a dermatologically acceptable carrier, wherein the ester is represented by the general formula 1:

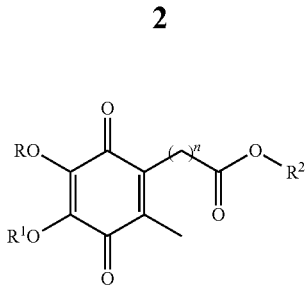

wherein R and $R^1$ are each independently a $C_1$-$C_4$ alkyl, $R^2$ is a $C_6$-$C_{22}$ alkyl, $C_6$-$C_{22}$ alkenyl, $C_6$-$C_{20}$ dienyl, $C_6$-$C_{22}$ trienyl, $C_8$-$C_{22}$ tetraenyl or a mixture thereof, and n is 2-18.

Another embodiment concerns a process for preparing an ester comprising:

a) reacting an acid, anhydride, or acid derivative of formula 2:

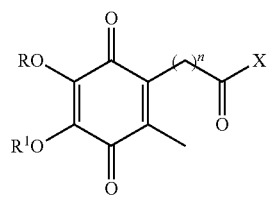

wherein X is —OH, —SH, —F, —Cl, —Br, —I, or —$OR^3$; and R and $R^1$ are each independently a $C_1$-$C_4$ alkyl; and n is 2-18; and wherein $R^3$ is $C_1$-$C_6$-alkyl or substituted $C_1$-$C_6$-alkyl.

with an alcohol of formula 3:

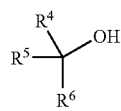

wherein $R^4$, $R^5$, and $R^6$ are each an aliphatic hydrocarbons containing from about 6 to about 22 carbons in the presence of an organic solvent to form at least on ester; and b) isolating said at least one ester.

Still another embodiment concerns a method for treating a skin condition comprising applying an effective amount of the composition according to claim 1 to skin.

BRIEF DESCRIPTION OF THE FIGURE

The FIGURE shows a graph which shows the cytotoxicity of different idebenone acid esters.

DETAILED DESCRIPTION OF THE INVENTION

The present invention concerns a series of novel esters and compositions containing the esters which are represented by the general formula 1:

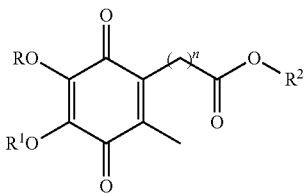

wherein R and $R^1$ are selected from branched- and straight-chain $C_1$-$C_4$ alkyl, $R^2$ is selected from substituted and unsubstituted, branched- and straight-chain saturated $C_6$-$C_{22}$ alkyl, substituted and unsubstituted, branched- and straight-chain $C_6$-$C_{22}$ alkenyl, substituted and unsubstituted, branched- and straight-chain $C_6$-$C_{20}$ dienyl, substituted and unsubstituted, branched- and straight-chain $C_6$-$C_{22}$ trienyl, and substituted and unsubstituted, branched- and straight-chain $C_8$-$C_{22}$ tetraenyl or mixtures thereof, and n is 2-18.

The alkyl, alkenyl, dienyl, trienyl, and tetraenyl groups which may be represented by $R^2$ may be straight- or branched-chain aliphatic hydrocarbons containing up to about 22 carbon atoms and may be substituted, for example, with one to three groups selected from $C_1$-$C_6$-alkoxy, cyano, $C_2$-$C_6$-alkoxycarbonyl, $C_2$-$C_6$-alkanoyloxy, hydroxy, aryl, heteroaryl, thiol, thioether, and halogen. The terms "$C_1$-$C_6$-alkoxy", "$C_2$-$C_6$-alkoxycarbonyl", and "$C_2$-$C_6$-alkanoyloxy" are used to denote organic functionality corresponding to the structures —$OR^3$, —$CO_2R^3$, and —$OCOR^3$, respectively, wherein $R^3$ is $C_1$-$C_6$-alkyl or substituted $C_1$-$C_6$-alkyl.

The esters can be prepared by the reaction of an acid, anhydride, or acid derivative of formula 2:

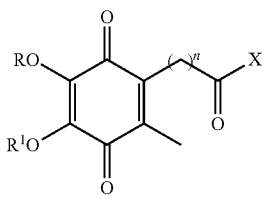

wherein X is —OH, —SH, —F, —Cl, —Br, —I, or —$OR^3$; and R and $R^1$ are selected from branched- and straight-chain $C_1$-$C_4$ alkyl; and n is 2-18; wherein $R^3$ is $C_1$-$C_6$-alkyl or substituted $C_1$-$C_6$-alkyl.
with an alcohol of formula 3:

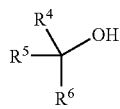

wherein $R^4$, $R^5$, and $R^6$ may each be straight- or branched-chain aliphatic hydrocarbons containing up to about 22 carbon atoms, for from about 6 to about 22 carbons, and may be substituted, for example, with one to three groups selected from $C_1$-$C_6$-alkoxy, cyano, $C_2$-$C_6$-alkoxycarbonyl, $C_2$-$C_6$-alkanoyloxy, hydroxy, aryl, heteroaryl, thiol, thioether, and halogen. The terms "$C_1$-$C_6$-alkoxy", "$C_2$-$C_6$-alkoxycarbonyl", and "$C_2$-$C_6$-alkanoyloxy" are used to denote organic functionality corresponding to the structures —$OR^3$, —$CO_2R^3$, and —$OCOR^3$, respectively, wherein $R^3$ is $C_1$-$C_6$-alkyl or substituted $C_1$-$C_6$-alkyl.

In an embodiment, the process comprises the reaction of a compound represented by formula 2 with 3 in the presence of an organic solvent; varying reaction times may be required and can be determined by those of ordinary skill in the art. The process is carried out in an organic solvent such as an inert solvent chosen from cyclic or acyclic ether solvents such as diethyl ether, diisopropyl ether, tert-butyl methyl ether, or tetrahydrofuran, aromatic hydrocarbons such as benzene, toluene, or xylene, aliphatic or alicyclic saturated or unsaturated hydrocarbons such as hexane, heptane, cyclohexane, or limonene, halogenated hydrocarbons such as dichloromethane, dichloroethane, dibromoethane, tetrachloroethylene, or chlorobenzene, polar aprotic solvents such as acetonitrile, dimethyl formamide, or dimethyl sulfoxide, or mixtures thereof. The process may be carried out at a temperature between about −100° C. and the boiling point of the solvent, or between about 0-60° C., or even between about 20-50° C. Alternatively, an enzyme with or without methods for the removal of water may also be utilized. The enzyme used in the process is chosen from a protease, a lipase, or an esterase. For example, lipases may be used and may be in the form of whole cells, isolated native enzymes, or immobilized on supports. Examples of these lipases include but are not limited to Lipase PS "Amano" (from *Pseudomonas* sp), Lipase PS-C "Amano" (from *Psuedomonas* sp immobilized on ceramic), Lipase PS-D "Amano" (from *Pseudomonas* sp immobilized on diatomaceous earth), LipoPrime® 50T, Lipozyme® TL IM, or Novozym® 435 (from *Candida antarctica* immobilized on acrylic resin).

The process may optionally be carried out in the presence of various addenda chosen from molecular sieves or ion exchange resins. For example, 3A, 4A, or 5A molecular sieves can be used. The product(s) of the process may be isolated using methods known to those of skill in the art, e.g., extraction, filtration, or crystallization. The product 1 may be purified if necessary using methods known to those of skill in the art, e.g., extraction, chromatography, distillation, or crystallization.

The esters according to the present invention can be used in compositions, such as cosmetic compositions, skin care compositions and the like. The compositions can be useful, for example, for reducing skin roughness, fine lines, and wrinkles, improving photo-damaged skin, regenerating skin, reducing skin hyper-pigmentation, and reducing irritation and/or inflammatory reaction in skin.

Typical cosmetic and/or skin care compositions of the invention contain at least 0.001% by weight of the esters according to the present invention. For example, the compositions can contain from about 0.001% to about 10.0% by weight or from about 0.01% to about 5.0% by weight of the esters according to the present invention. Lower concentrations may be employed for less pronounced conditions, and higher concentrations may be employed with more acute conditions. Suggested ranges also depend upon any adjunct ingredients employed in the compositions.

The cosmetic and skin care compositions of the invention may also contain other skin conditioning ingredients in addition to esters. Such compositions may also contain other skin ingredients such as tetronic acid, tetronic acid derivatives, hydroquinone, kojic acid, 4-hydroxybenzyl alcohol, gallic acid, arbutin, α-hydroxyl acids, and fatty acid esters of ascorbic acid. Such other ingredients are known to those of skill in the art.

Typically, topical application to skin sites is accomplished in association with a carrier. Where employed, the carrier is inert in the sense of not bringing about a deactivation or oxidation of active or adjunct ingredient(s), and in the sense of not bringing about any adverse effect on the skin areas to which it is applied. For example, the compounds according to the present invention are applied in admixture with a dermatologically acceptable carrier or vehicle (e.g., as a lotion, cream, ointment, soap, stick, or the like) so as to facilitate topical application and, in some cases, provide additional beneficial effects as might be brought about, e.g., by moisturizing of the affected skin areas. Many preparations are known in the art, and include lotions containing oils and/or alcohols and emollients such as olive oil, hydrocarbon oils and waxes, silicone oils, other vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids.

EXAMPLES

This invention can be further illustrated by the following examples, although it will be understood that these examples are included merely for purposes of illustration and are not intended to limit the scope of the invention unless otherwise specifically indicated.

Preparation of Idebenone acid: 10-(4,5-dimethoxy-2-methyl-3,6-dioxocyclohexa-1,4-dienyl)decanoic acid; Jones Reagent was freshly prepared as follows: $CrO_3$ (12.5 g) diluted with concentrated $H_2SO_4$ (12.5 mL) was mixed and carefully added to ice cold water (37.5 mL); the contents were mixed and allowed to warm to room temperature. Idebenone (2.50 g, 7.39 mmol) was weighed out into a 250 mL round bottom flask containing a stir-bar. Acetone (100 mL) was then added drop-wise and mixed to afford a bright orange solution. While stirring at room temperature, Jones reagent was added and the reaction was monitored via $SiO_2$ TLC. Additional Jones reagent was added until TLC suggested that oxidation was complete ($t_R$ shift of ~0.50 to ~0.62; 1:1 EtOAc:Hexane). The crude material was concentrated under reduced pressure and then purified by $SiO_2$ chromatography. Product only fractions were combined and concentrated under reduced pressure and further dried under a vacuum line to afford 2.15 g of orange solid; 83% yield. $^1H$ NMR (300 MHz; DMSO-$d_6$) δ 11.95 (bs, 1H; disappears with the addition of $D_2O$), 3.87 (s, 6H; —OMe), 2.41-2.36 (m, 2H), 2.36-2.30 (t, 2H), 1.92 (s, 3H), 1.52-1.46 (m, 2H), 1.31-1.19 (bs, 12H); $^{13}C$ NMR (75 MHz; DMSO-$d_6$) 184.0, 183.5, 174.5, 144.3, 144.2, 141.9, 138.2, 60.7, 33.7, 29.2, 28.8, 28.7, 28.6, 28.1, 25.7, 24.5, 11.6.

Preparation of Idebenone Carboxylates

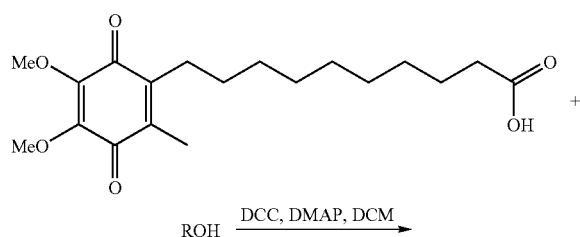

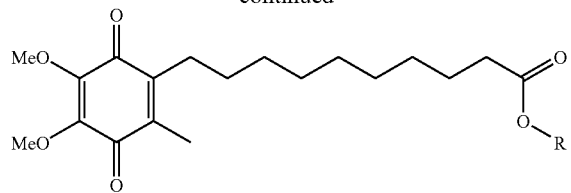

General Procedure:
Idebenone acid (6.6 mmol), alkyl alcohol (6.0 mmol), 4-(dimethylamino)pyridine (DMAP) (1.2 mmol) were dissolved in $CH_2Cl_2$ (40 mL) at room temperature then N,N'-dicyclohexylcarbodiimide (DCC) (6.6 mmol) was added portionwise. The reaction mixture turned cloudy in 5 min. and was stirred overnight. The resulting mixture was filtered through a Celite pad and washed with hexanes to give a yellow solution, which was concentrated in vacuo. The residue was purified by passing through a short silica gel filtration column with 5%~15% EtOAc in Hexanes to give an orange solid or oil.

Geranyl Idebenone Carboxylate (286-001): Orange oil, 65% yield. $^1H$ NMR (CDCl$_3$) δ (ppm): 1.2-1.4 (m, 12H), 1.60 (s, 3H), 1.6-1.7 (m, 2H), 1.68 (s, 3H), 1.70 (s, 3H), 2.01 (s, 3H), 2.1-2.2 (m, 4H), 2.30 (t, 2H, J=7.2 Hz), 2.45 (t, 2H, J=7.2 Hz), 3.99 (s, 6H), 4.59 (d, 2H, J=7.5 Hz), 5.04-5.12 (m, 1H), 5.30-5.38 (m, 1H). $^{13}C$ NMR (CDCl$_3$) δ (ppm): 25.2, 25.9, 26.5, 26.6, 28.9, 29.3, 29.4, 29.5, 30.0, 31.1, 34.5, 39.7, 61.32, 61.36, 118.6, 123.9, 132.0, 138.8, 142.3, 143.2, 144.5, 174.1, 184.3, 184.9.

Cetyl Idebenone Carboxylate (286-002): Orange solid, 65% yield. $^1H$ NMR (CDCl$_3$) δ (ppm): 0.8-0.9 (m, 3H), 1.2-1.4 (m, 38H), 1.55-1.65 (m, 4H), 2.01 (s, 3H), 2.29 (t, 2H, J=7.5 Hz), 2.45 (t, 2H, J=7.5 Hz), 3.987 (s, 3H), 3.990 (s, 3H), 4.05 (t, 2H, J=6.9 Hz). $^{13}C$ NMR (CDCl$_3$) δ (ppm): 12.0, 22.8, 25.2, 26.1, 26.6, 28.8, 28.9, 29.3, 29.41, 29.45, 29.5, 29.6, 29.72, 29.77, 29.85, 29.87, 29.89, 30.0, 31.8, 34.5, 61.3, 64.6, 138.8, 143.2, 144.5, 174.1, 184.3, 184.8.

Stearyl Idebenone Carboxylate (286-003): Orange solid, 89% yield. $^1H$ NMR (CDCl$_3$) δ (ppm): 0.88 (t, 3H, J=6.6 Hz), 1.2-1.4 (m, 42H), 1.55-1.65 (m, 4H), 2.01 (s, 3H), 2.28 (t, 2H, J=7.5 Hz), 2.45 (t, 2H, J=7.5 Hz), 3.987 (s, 3H), 3.990 (s, 3H), 4.05 (t, 2H, J=6.9 Hz). $^{13}C$ NMR (CDCl$_3$) δ (ppm): 12.0, 25.1, 26.1, 26.1, 26.5, 28.8, 28.9, 29.27, 29.38, 29.42, 29.46, 29.53, 29.70, 29.74, 29.87, 29.95, 34.5, 61.2, 64.5, 138.8, 143.2, 144.4, 174.0, 184.2, 184.8.

Decyl Idebenone Carboxylate (286-004): Orange solid, 78% yield. $^1H$ NMR (CDCl$_3$) δ (ppm): 0.88 (t, 3H, J=6.6 Hz), 1.2-1.4 (m, 26H), 1.55-1.65 (m, 4H), 2.01 (s, 3H), 2.29 (t, 2H, J=7.5 Hz), 2.45 (t, 2H, J=7.5 Hz), 3.990 (s, 3H), 3.993 (s, 3H), 4.07 (t, 2H, J=6.9 Hz). $^{13}C$ NMR (CDCl$_3$) δ (ppm): 11.8, 25.0, 26.0, 26.4, 28.68, 28.72, 29.1, 29.24, 29.27, 29.32, 29.54, 29.8, 31.6, 34.3, 61.0, 64.3, 138.6, 143.0, 144.3, 173.8, 184.0, 184.6.

Hexyl Idebenone Carboxylate (286-005): Orange oil, 76% yield. $^1H$ NMR (CDCl$_3$) δ (ppm): 0.88 (m, 3H), 1.2-1.4 (m, 18H), 1.55-1.65 (m, 4H), 2.00 (s, 3H), 2.29 (m, 2H), 2.44 (t, 2H, J=6.6 Hz), 3.99 (m, 6H), 4.05 (tt, 2H, J=6.9, 1.2 Hz). $^{13}C$ NMR (CDCl$_3$) δ (ppm): 12.1, 14.2, 25.2, 25.8, 26.6, 28.8, 28.9, 29.3, 29.41, 29.49, 30.0, 34.6, 61.3, 64.6, 138.8, 143.2, 144.5, 174.1, 184.3, 184.8.

Farnesyl Idebenone Carboxylate (286-006): Orange oil, 80% yield. $^1H$ NMR (CDCl$_3$) δ (ppm): 1.2-1.4 (m, 12H), 1.60 (s, 6H), 1.6-1.8 (m, 2H), 1.68 (s, 3H), 1.70 (s, 3H), 2.01 (s, 3H), 1.9-2.2 (m, 8H), 2.30 (m, 2H), 2.45 (t, 2H, J=7.2 Hz), 3.987 (s, 3H), 3.990 (s, 3H), 4.59 (d, 2H, J=6.9 Hz), 5.05-5.15

(m, 2H), 5.3-5.4 (m, 1H). $^{13}$C NMR (CDCl$_3$) δ (ppm): 11.9, 16.0, 16.5, 17.7, 25.0, 25.7, 26.2, 26.4, 26.7, 28.7, 29.1, 29.2, 29.3, 29.8, 31.6, 34.4, 39.5, 39.7, 61.13, 61.18, 118.5, 124.3, 131.3, 135.6, 135.8, 138.7, 142.1, 142.5, 143.0, 144.3, 173.9, 184.1, 184.7.

Butyl Idebenone Carboxylate (286-007): Orange oil, 73% yield. $^1$H NMR (CDCl$_3$) δ (ppm): 0.88 (dt, 3H, J=1.8, 7.5 Hz), 1.2-1.4 (m, 14H), 1.55-1.65 (m, 4H), 1.96 (s, 3H), 2.23 (t, 2H, J=7.5 Hz), 2.44 (m, 2H), 3.99 (m, 6H), 4.05 (dt, 2H, J=1.8, 6.9 Hz): $^{13}$C NMR (CDCl$_3$) δ (ppm): 12.4, 14.3, 19.7, 25.5, 26.9, 29.3, 29.6, 29.76, 29.85, 30.3, 31.3, 34.9, 61.7, 64.6, 139.2, 143.6, 144.8, 174.5, 184.7, 185.2.

Mixed Fatty ($C_{16}$-$C_{18}$-$C_{20}$) Idebenone Carboxylate (286-008): Orange oil, 74% yield. $^1$H NMR (CDCl$_3$) δ (ppm): 0.86 (m, 3H), 1.2-1.4 (m, 14H), 1.55-1.65 (m, 4H), 1.99 (s, 3H), 2.28 (t, 2H, J=7.5 Hz), 2.43 (m, 2H), 3.95 (m, 2H), 3.971 (s, 3H), 3.974 (s, 3H). $^{13}$C NMR (CDCl$_3$) δ (ppm): 12.0, 14.2, 22.76, 22.78, 25.1, 26.5, 26.77, 26.80, 28.8, 29.2, 29.37, 29.42, 29.46, 29.66, 29.70, 29.75, 29.9, 30.1, 31.4, 31.9, 32.0, 34.5, 37.4, 61.2, 67.1, 138.7, 143.1, 144.4, 174.2, 184.2, 184.8.

Enzyme catalyzed formation of Farnesyl Idebenone Carboxylate:

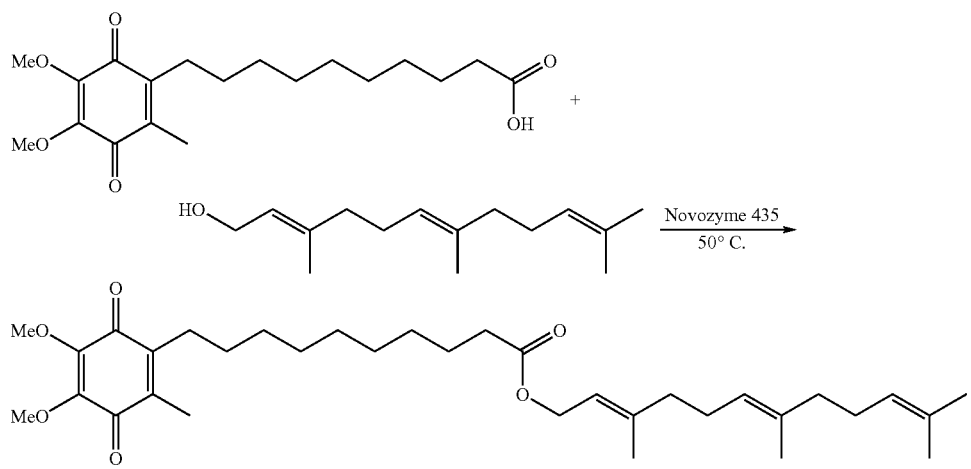

Idebenone acid (1.06 g, 3.0 mmol), farnesol (669 mg, 3.0 mmol), and Novozyme (35 mg) were mixed in a conical tube then heated (50° C.) with N$_2$ bubbling through the mixture. After overnight heating and bubbling, the mixture was purified by passing through a short silica gel filtration column with 5%~15% EtOAc in Hexanes to give the orange oil (1.46 g, 87%). $^1$H and $^{13}$C NMR match those of the chemically prepared product (see above).

Probing Inherent Cytotoxicity:

Melanocytes (B16:F10 mouse melanoma cells) were purchased from ATCC (American Type Culture Collection; Manassas, Va.). Cells were grown at ~37° C. in DMEM (Dulbecco's Modified Eagle's Medium) without phenol red, and in the presence of 10% FCS (fetal calf serum) with 1% antibiotics/antimycotics (Gibco #15240). Upon becoming confluent (~90%), cells were detached with trypsin-EDTA and counted.

MTT Screening: Cells (5×10$^5$ cells/well) were plated into 96 well plates (Corning/Costar #3595) using a volume of 100±1 µL medium/well. Twenty-four h after initially plating, each compound tested was freshly prepared in DMSO. The general procedure was as follows: stock solution was diluted in culture medium to give concentrations of 2.0, 20, 40, 100 and 200 µM; DMSO concentrations were consistently kept at ≦0.4%. Next, 100 µL of each dilution was added to the existing 100 µL/well culture medium rendering final concentrations of 1.0, 10, 20, 50 and 100 µM per well, n=8. At 72 h post-dose, 10% MTT (3-[4,5-dimethylthiazol-2-yl]-2,5-diphenyl tetrazolium bromide) solution (20 µL; 5.0 mg/mL in DMEM without phenol red) was added to each well. MTT allows one to measure the viability (cell growth determination) of living cells as a function of mitochondrial dehydrogenase activity (for example, see DeMarco et al., *Biochem. Pharmacol.* 2002, 64, 1503-1512). The plate was incubated for 2 h at ~37° C. Medium was carefully removed and MTT solvent solution (200 µL; 0.1 N HCl in anhydrous isopropanol) was added to each well. Using a Molecular Devices Spectra Max 340 (Sunnyvale, Calif.), the 96-well plate was shaken (10 min) and subsequently read using an absorbance wavelength (570 nm) with a subtracted background absorbance (690 nm). Microsoft Excel, Chem-Draw (version 9.0.7), and Prism 5.01™ (GraphPad Software, Inc.; San Diego, Calif.) were used to compile the raw data, draw the chemical structures, and process the experimental data, respectively.

As summarized in FIG. 1, the 72 h MTT data helps to illustrate that different idebenone acid esters have intrinsic differences in their cytotoxicity.

The invention has been described in detail with particular reference to preferred embodiments thereof, but it will be understood that variations and modifications can be effected within the spirit and scope of the invention.

We claim:

1. A composition, comprising an ester and a dermatologically acceptable carrier, wherein the ester is represented by the general formula 1:

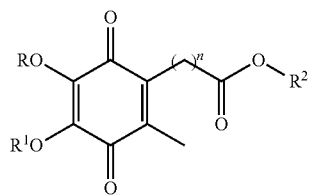

1 wherein R and R$^1$ are each independently a C$_1$-C$_4$ alkyl, R$^2$ is a C$_6$-C$_{22}$ alkyl, C$_6$-C$_{22}$ alkenyl, C$_6$-C$_{20}$ dienyl, C$_6$-C$_{22}$ trienyl, C$_8$-C$_{22}$ tetraenyl or a mixture thereof, and n is 2-18.

2. The composition according to claim 1, wherein the ester is present in an amount of at least 0.001% by weight.

3. The composition according to claim 2, wherein the ester is present in an amount of from about 0.001% to about 10% by weight.

4. The composition according to claim 3, wherein the ester is present in an amount of from about 0.01% to about 5.0% by weight.

5. The composition according to claim 1, wherein the alkyl, alkenyl, dienyl, trienyl, and tetraenyl group of R$^2$ is an aliphatic hydrocarbon.

6. The composition according to claim 5, wherein the aliphatic hydrocarbon is substituted with one to three groups selected from the group consisting of C$_1$-C$_6$-alkoxy, cyano, C$_2$-C$_6$-alkoxycarbonyl, C$_2$-C$_6$-alkanoyloxy, hydroxy, aryl, heteroaryl, thiol, thioether, and halogen.

7. The composition according to claim 1, wherein the composition is a lotion, a cream, a gel, an ointment, soap, or a stick.

* * * * *